(12) United States Patent
Mersky (10) Patent No.: US 9,301,061 B2
(45) Date of Patent: *Mar. 29, 2016

(54) SYSTEM AND METHOD FOR MEASURING AND RECORDING SKULL VIBRATION IN SITU

(71) Applicant: Audiodontics, LLC, Bethesda, MD (US)

(72) Inventor: Barry L. Mersky, Highland, MD (US)

(73) Assignee: Audiodontics, LLC, Bethesda, MD (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/745,319

(22) Filed: Jan. 18, 2013

(65) Prior Publication Data

US 2013/0131437 A1    May 23, 2013

Related U.S. Application Data

(63) Continuation of application No. 12/759,206, filed on Apr. 13, 2010, now Pat. No. 8,376,967.

(51) Int. Cl.
*A61B 5/11* (2006.01)
*A61B 5/00* (2006.01)
*H04R 25/00* (2006.01)

(52) U.S. Cl.
CPC ............... *H04R 25/604* (2013.01); *A61B 5/11* (2013.01); *A61B 5/682* (2013.01); *H04R 25/48* (2013.01)

(58) Field of Classification Search
CPC ............................ H04R 25/604; H04R 25/48
See application file for complete search history.

(56) References Cited

U.S. PATENT DOCUMENTS

| | | |
|---|---|---|
| 2,995,633 A | 8/1961 | Puharich |
| 3,440,314 A | 4/1969 | Frisch |
| 4,096,637 A | 6/1978 | Stade |
| 4,150,262 A | 4/1979 | Ono |
| 4,629,424 A | 12/1986 | Lauks |
| 5,033,999 A | 7/1991 | Mersky |
| 5,074,310 A | 12/1991 | Mick |
| 5,326,349 A | 7/1994 | Baraff |
| 5,447,489 A | 9/1995 | Issalene et al. |
| 5,455,842 A | 10/1995 | Mersky |
| 5,460,593 A | 10/1995 | Mersky et al. |
| 5,558,091 A | 9/1996 | Acker et al. |
| 5,579,284 A | 11/1996 | May |
| 5,730,151 A | 3/1998 | Summer |

(Continued)

FOREIGN PATENT DOCUMENTS

WO    WO 2005000391    6/2005

OTHER PUBLICATIONS

Hodgetts et al. (2010) "A comparison of three approaches to verifying aided Baha output," Int. J. Audio., 49(4):286-95.

(Continued)

*Primary Examiner* — Sean Dougherty
(74) *Attorney, Agent, or Firm* — William C. Schrot; AuerbachSchrot LLC (57) ABSTRACT

A method and apparatus for recording and measuring in-situ skull vibration includes a receiving means, a transducer mounted into or unto the receiving means and capable of transducing mechanical vibration within the dental bone conduction pathway into electrical signals, and extra-oral recordation hardware and software capable of receiving and processing the electrical signals from the transducer.

24 Claims, 5 Drawing Sheets

(56) References Cited

U.S. PATENT DOCUMENTS

| | | |
|---|---|---|
| 5,769,891 A | 6/1998 | Clayton |
| 5,951,292 A | 9/1999 | Lee |
| 6,009,878 A | 1/2000 | Weijand et al. |
| 6,047,163 A | 4/2000 | Miyoshi |
| 6,239,705 B1 | 5/2001 | Glen |
| 6,394,969 B1 | 5/2002 | Lenhardt |
| 6,463,157 B1 | 10/2002 | May |
| 6,473,512 B1 | 10/2002 | Juneau et al. |
| 6,823,195 B1 | 11/2004 | Boesen |
| 6,961,623 B2 | 11/2005 | Prochazka |
| 7,043,040 B2 | 5/2006 | Westerkull |
| 7,072,718 B2 | 7/2006 | Von Arx et al. |
| 7,153,257 B2 | 12/2006 | Schneider et al. |
| 7,269,266 B2 | 9/2007 | Anjanappa et al. |
| 7,447,319 B2 | 11/2008 | Miller et al. |
| 7,486,798 B2 | 2/2009 | Anjanappa et al. |
| 7,796,769 B2 | 9/2010 | Abolfathi |
| 7,945,068 B2 | 5/2011 | Abolfathi et al. |
| 2002/0026091 A1 | 2/2002 | Leysieffer |
| 2007/0123796 A1 | 5/2007 | Lenhardt et al. |
| 2009/0022351 A1 | 1/2009 | Wieland et al. |
| 2009/0048508 A1 | 2/2009 | Gill et al. |
| 2009/0270673 A1 | 10/2009 | Abolfathi et al. |
| 2009/0274325 A1 | 11/2009 | Abolfathi |
| 2009/0281433 A1 | 11/2009 | Saadat et al. |
| 2010/0272299 A1 | 10/2010 | Van Schuylenbergh et al. |
| 2011/0007920 A1 | 1/2011 | Abolfathi et al. |
| 2011/0015466 A1 | 1/2011 | Waldmann |

OTHER PUBLICATIONS

Laitakari et.al. (1995) "Objective Real Ear Measurements of Bone-conduction hearing Aid Performance," Scan. Audio., 24:53-56.

Laitakari, K, Jamsa T. (2001) "Computerized in-situ test for bone conduction hearing aids," Scan. Audio., 30(Suppl 52):79-80.

Mersky, B.L., Technical Report for US Army, SBIR Phase 1, Human Communication Performance in High Noise Environments, Contract DAAD17-00-C-0076, Dec. 22, 2000.

Mersky, B.L., Technical Report for US Army, SBIR Option Phase 1, Human Communication Performance in High Noise Environments, Contract DAAD17-00-C-0076, May 23, 2003.

Majdalawieh O. et al. (2006) "Output Vibration Measurements of Bone-Anchored Hearing Aids," Otology & Neurotology 27:519-530.

Brouns A.J. (1971) "Experimental Wide-Bandwidth Tooth-Contact Microphone," J. Audio Engineer. 9:41-45.

Acker-Mills B. et al. (2005) "*Speech Intelligibility with Acoustic and Contact Microphones*," New Directions for Improving Audio Effectiveness 7-1-7-14.

Ishihara M, Shirataki J (2005) "*Applying Multi-level Sliced Speech Signals to Bone-conducted Communication*," Circuits and Systems 3:2735-2738.

SYSTEM AND METHOD FOR MEASURING AND RECORDING SKULL VIBRATION IN SITU

CROSS REFERENCE TO RELATED APPLICATION AND CLAIM TO PRIORITY

The present application is a continuation of U.S. application Ser. No. 12/759,206, filed Apr. 13, 2010, now U.S. Pat. No. 8,376,967, the disclosure of which is incorporated herein by reference and to which priority is claimed.

STATEMENT REGARDING FEDERALLY SPONSORED RESEARCH OR DEVELOPMENT

This invention was supported by the National Institute of Deafness and Communication Disorders (DIDCD) as provided for by the terms of 1R41DC010082-01A1. The United States government has certain rights in the invention.

FIELD OF THE INVENTION

This invention relates to a system or apparatus for measuring and recording skull vibration in situ comprising a receiving means which engages at least one maxillary tooth; a dental material which is capable of filling any gaps between the receiving means and the tooth (or teeth), and, is capable of transmitting mechanical vibration that exist within the dental bone conduction pathway to the receiving means. The invention further comprises a transducer or sensor mounted into or unto the receiving means, said sensor being capable of transducing mechanical vibration into electrical signals and an extra-orally disposed signal conditioner, computer, and other data recorder hardware and software for receiving and processing electrical signals from the transducer.

BACKGROUND OF THE INVENTION

Reliable, non-invasive, low-cost, in situ measurement of skull vibration for the purpose of fitting a bone conduction hearing aid currently is not possible. (Hodgetts W. E, Hakansson B. E. V, Hagler P, Soli S, "A comparison of three approaches to verifying aided Baha output," *Internl J Audiology* 2009 online.)

Skin placement of an accelerometer as a means to record skull vibration (specifically stimulation created by an implanted bone vibrator) was attempted by Laitakari, et. al. (Laitakari k, Lopponen H, Salmivalli A, Sorri M, "Objective Real Ear Measurements of Bone-conduction hearing Aid Performance," *Scan Audiol* 24:53-6, 1995; Laitakari K, Jamsa T., "Computerized in-situ test for bone conduction hearing aids," *Scand Audiol:* 30: Suppl 52:79-80, 2001.)

This method uses a typical mechanical headband, like those associated with the oscillators for bone conduction audiometry, to couple the accelerometer to the skull. Currently, it is acknowledged by experts in the field that because vibrations of the overlying skin do not reflect underlying skull vibrations, with the existing art, it is almost impossible to measure skull vibration in living subjects. (Majdalawieh, Osama, Abstract to PhD Thesis, Dalhousie University, Halifax, Canada 2008.)

Miller U.S. Pat. No. 7,447,319—"Method and system for external assessment of hearing aids that include implanted actuators" focused on the output of the hearing aid into an electrical/mechanical detector. A similar approach was taught by Leysieffer in U.S. Patent Application Publication No. 2002/0026091, "Implantable hearing system with means for measuring its coupling quality." Both of these inventions were not concerned about the in-situ output in a living skull, but rather the output into a device which functions more or less as a "simulator device."

The dental bone conduction pathway as used herein should be considered a sub-pathway of the non-acoustic "bone conduction pathway" for sound transmission to the hearing nerve. In the dental bone conduction pathway, sound perceived at the hearing nerve originates in structures of the mouth and pharynx. Speech sounds and chewing sounds, for example, travel to the hearing nerve via the dental bone conduction pathway. By contrast, loud ambient helicopter noise that penetrates the skin over the entire skull, neck, and body can be considered noise arriving at the hearing nerve via the bone conduction pathway. Similarly, standard bone conduction audiometry with skull stimulation at the mastoid or forehead uses the bone conduction pathway as distinct from the dental bone conduction pathway.

The distinction between pathways is important because of anatomical differences between the pathways. The bio-mechanical forces in the dental bone conduction pathway are variable and thus may create variable results when compared to stimulation of structures elsewhere on the skull (at the mastoid or forehead for example). The large resonant chamber, anatomically named as the mouth and oropharynx, has its resonance frequency altered by combinations of opening the mouth and movements of the tongue, lips, and vocal chords (human speech). The mere act of biting changes the mechanical load on a top tooth by significantly increasing the load on that top tooth with the effective mass (and variable biting force) from the lower jaw. Other pathway entrances on the skull do not contain such variable effective mass or compliant muscles and ligaments. Also, those other skull areas have far less voluntary muscle and compliant soft tissue (when compared to the tongue and cheeks of the mouth, for example), and more fixed chambers (e.g., frontal sinuses, mastoid air cells, external ear canal), and thus necessarily have more consistent volumes, mechanical loads, and input mechanical point impedances than do structures of the mouth and pharynx; that is, structures comprising the dental bone conduction pathway.

Unlike other methods to record (non-acoustic) skull vibration, the instant invention uses the teeth as the site for measuring skull vibrations. Use of the teeth allows for greater sensitivity because vibration sensing is via the dental bone conduction pathway having no overlying skin, muscle, etc., to affect skull vibration. Equally important, measuring skull vibrations through the teeth allows for repeatable and reproducible tooth placement with a concomitant replication of the (original) coupling force. The use of a tooth microphone for speech recording and voice communication has been taught by Brouns (Brouns J R, "Experimental wide-band tooth-contact microphone," *J Audio Engineer.* 9:1:42, 1971); Mersky (U.S. Pat. No. 5,455,842—Underwater Communication System); Anajanappa (U.S. Pat. Nos. 7,269,266; 7,486,798); May (U.S. Pat. No. 5,579,284); Wieland (U.S. Patent Application Publication No. 2009/002235107), and others. The tooth coupling methodologies, associated electronics, and recording software differs substantially from the means and methods taught in this invention. Other art by Saadat and Alboufathi (U.S. Patent Application Publication No. 2009/0281433, "Systems and methods for pulmonary monitoring and treatment") teaches a means and method for recording breath sounds using an intraoral sensor. That art differs from the instant invention in that it requires an impression of the patient's dentition in order to fabricate and customize the tooth attachment means.

SUMMARY OF THE INVENTION

Accordingly, it is one object of the invention to provide an apparatus for recording and measuring in-situ skull vibration comprising a receiving means which simultaneously engages the undercut area in the gingival one-third of at least one maxillary tooth and the interproximal area between two adjacent maxillary teeth on both the buccal and lingual surfaces, a transducer mounted into or unto the receiving means, said transducer capable of transducing mechanical vibration within a dental bone conduction pathway into electrical signals; and recordation hardware and software capable of receiving and processing said electrical signals from said transducer.

It is another object of the invention to provide a method of placing a transducer in an apparatus for recording and measuring in-situ skull vibration, the method comprising the steps of selecting a receiving means that simultaneously engages the undercut area in the gingival one-third of at least one maxillary tooth and the interproximal area between two adjacent maxillary teeth, engaging said tooth and teeth on both the buccal and lingual surfaces; covering said transducer with a sheath and placing the covered transducer into said receiving means; and connecting said transducer via a wire to a recording system disposed outside the mouth for recording electrical signals produced by the transducer.

It is yet another object of the invention to provide a method of placing a transducer in an apparatus for recording and measuring in-situ skull vibration, the method comprising the steps of selecting a metallic receiving means capable of holding said transducer in intimate contact with said receiving means and at least one teeth; filling said receiving means with a dental material capable of filling any gaps between said receiving means and said at least one natural tooth, said material being capable of setting to a sufficiently rigid state in the undercut area in the gingival one-third of at least one maxillary tooth and the interproximal area between two adjacent maxillary teeth, with said material being able to compress sufficiently to allow the release and removal of said means from the mouth, said material being capable of transmitting mechanical vibration within the dental bone conduction pathway to the receiving means and transducer; connecting said transducer via a wire to a recording system disposed outside the mouth for recording electrical signals produced by the transducer.

The receiving means and the filler material constitute a tooth coupling assembly for engaging the transducer in intimate vibrational contact with at least one teeth and preferably no more than two posterior teeth in the upper arch (maxilla). The intimate vibrational contact is achieved through a spring-load created by the coupling assembly.

Optionally, the coupling assembly further comprises a retainer such as a metallic spring clip for biasedly retaining the receiving means in the undercut area in the gingival one-third of at least one maxillary tooth and the interproximal area between two adjacent maxillary teeth on both the buccal and lingual surfaces.

In one embodiment, the tooth coupling assembly comprises a receiving means configured like a shell or tray filled with a biocompatible filler material which fills the shell and when placed over the teeth, flows to conform to the teeth, and then hardens. Spring-load is created either by the external shell or tray, the biocompatible filler material used for customization, or in the preferred embodiment, a combination of a springy tray and (springy) compressible biocompatible filler material. As used herein, the terms, "mouth safe" and "biocompatible materials" are used interchangeably.

In another embodiment, the receiving means of the tooth coupling assembly is preferably a disposable, thin, springy-plastic fabricated from a plastic like PVC. Alternatively it could be a spring-metal design fabricated from a material like Nitinol. Alternatively, it can be a very "rigid" cast metal which, in certain circumstances, provides cost advantages for re-use between different persons after autoclaving.

The biocompatible filler material of the tooth coupling assembly preferably is a poly-vinyl siloxane (PVS) addition-type dental impression material with a hardness durometer of about 40 (Shore-D scale) such as R-Si-Line Metal Bite (R-dental, Hamburg, Germany). It can also be a more rigid setting material such as dental impression compound (e.g., Denture Impression Compound, Kerr Manufacturing, Romulus, Mich.). A preferred embodiment uses PVS because after it has chemically set, the PVS has sufficient compressibility to spring over the undercuts of the natural teeth. In addition, PVS can retain its "set memory" and detail for long periods of time if properly stored (at cool, room temperature). When or if dental compound is used instead of PVS, the receiving means is configured to flex or spring around the tooth undercuts. In either case, the tooth coupling assembly allows for repeatable placement and coupling force against the teeth over long periods of time, such as six-months or more.

In one embodiment, the transducer-sensor is of the piezoelectric type. Piezoelectric transducer designs of any physical size, sensitivity, and capability (two-axis, three axis, etc.) can be used with this system. Other types of transducer materials such as magnetostrictive, magnetoresistive, and voice coil are usable by the instant invention. However, to record skull acceleration, piezoelectric transducers is currently the most cost effective.

BRIEF DESCRIPTION OF THE DRAWINGS

In the drawings, wherein like reference numerals identify similar elements.

DETAILED DESCRIPTION OF THE INVENTION

Figure 1:
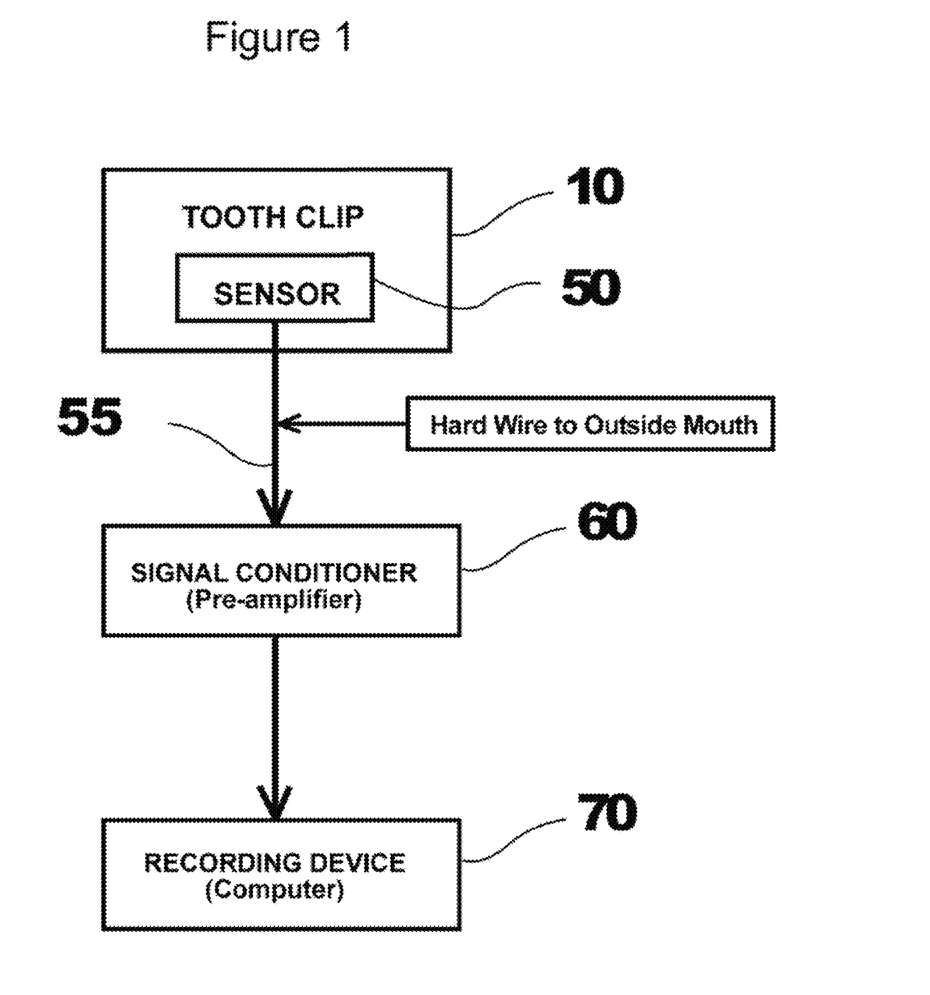
FIG. 1 is a process flow diagram of the method for recording and measuring in-situ skull vibration according to one embodiment of the present invention.

Referring now to the drawings of the present disclosure in which like numbers represent the same structure in the various views, FIG. 1 is a process flow schematic of the method for recording and measuring in-situ skull vibration according to one embodiment of the present invention. Elements 60 and 70 are companion electronic devices that match both the transducer or sensor 50 and the specific modality employed for recording skull vibrations. Software installed on the data recording device 70 will vary with the type of device (e.g., laptop computer, smartphone, etc.) and the diagnostic situation (e.g., the recordation of vibration created by a tooth or bone oscillator, or natural breath sounds existing within the dental bone conduction pathway). The modalities to be employed are within ready reach of one of skill in the art and it is understood that elements 60 and 70 can come in a wide variety of off the shelf configurations.

In a preferred embodiment, the recording software is configured to determine the in situ level of bone vibration created by skull stimulation from hearing aid systems which stimulates via the teeth. Also in an office or Clinic/hospital setting, where skull stimulation can occur from a calibrated audiometer bone oscillator, software specific to that audiometer and (hardware) setting can be written. It is also envisioned that during surgical procedure when an osseointegrated implant such as the Bone Anchored Hearing Aid (Cochlear Inc., Gothenburg Sweden) is being placed, initial recording of puretones with stimulation of the implant may be taken. Then after several months, the implant again may be stimulated and recordings made by the Invention, with the objective being to determine the implant stability through resonant frequency analysis (used in the field of implantology to determine the level of osseointegration achieved). Thus the particular software and hardware platform may differ depending on the measurement objective.

Accordingly, because of the repeatability of the instant methodology of measuring and recording in situ skull vibrations, degradation of hearing acuity and clinical changes related to hearing can be diagnosed. For example, in a hearing aid using an osseointegrated implant, if the person reports a decrease in hearing ability—the method of the instant invention can be used to assess whether the cause is due to a new nerve damage, or rather, damage to the implant or bone. Thus with the instant invention, the skull stimulation level (skull vibration levels) can be compared over time (through use of the same tooth-coupling assembly), leading to differential diagnosis.

Figure 2:
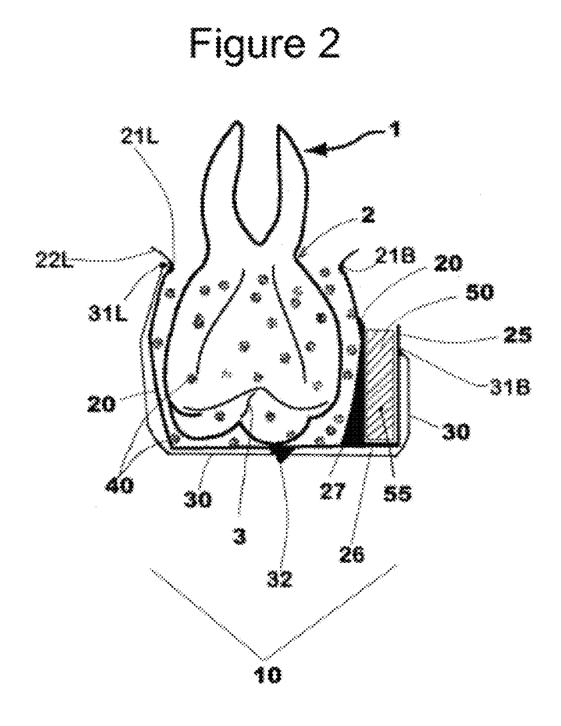
FIG. 2 illustrates the various embodiments of the tooth coupling assembly including the receiving means, transducer "side-car", transducer (accelerometer), and filler materials used for customization.

FIG. 2 illustrates the various embodiments of the tooth coupling assembly including the receiving means, transducer "side-car", transducer (accelerometer), and filler materials used for customization. The preferred embodiment of the tooth coupling assembly is placed over two adjoining teeth in the maxillary arch. The first preferred tooth covered is the maxillary first molar, and thus the second tooth covered would be the adjacent biscuspid (usually the $2^{nd}$ bicuspid, also known as the $2^{nd}$ premolar). FIG. 2 shows a "slice" view of the tooth coupling assembly slicing between the molar and bicuspid. It is preferred that the tooth coupling assembly be placed over no more than two teeth in order to minimize the mass of the assembly and to maintain the sensitivity of the attached accelerometer to low-amplitude vibration in the dental bone conduction pathway.

Figure 3:
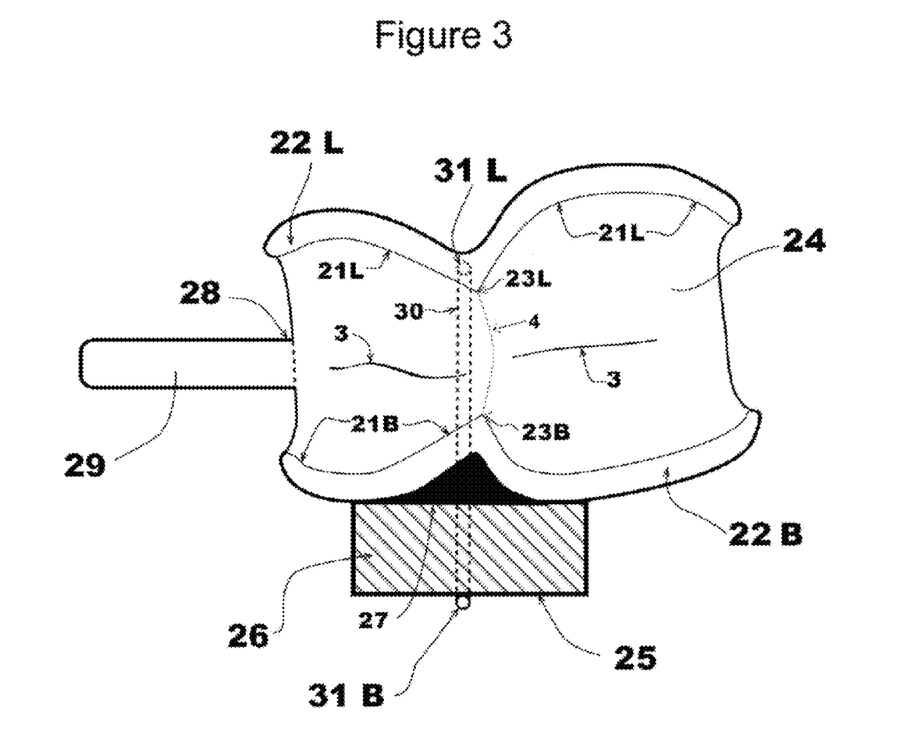
FIG. 3 illustrates a top-view of tooth coupling assembly including the "side-car". The transducer and biocompatible filler materials are absent.

Referring now to FIGS. 2 and 3, the tooth coupling assembly is placed over a tooth (molar) 1, having a cervical neck 2 (that constriction of an natural tooth which occurs at the point where the enamel meets the root; in vivo, this landmark is visible at or near the gum-line along the length of the tooth at the gum-line; it is an undercut area, relative to the clinical crown of the tooth), and a central groove 3 which runs in a mesial to distal, or front-of-mouth to back-of-mouth direction along the biting surface of the clinical crown usually in the center of the occlusal surface. Referring to FIG. 3, the interproximal area 4 that exists at the gum-line between two adjacent teeth is shown. When one uses dental floss, the floss is intended to clean the buccal-to-lingual area shown by the interproximal area 4 which is a naturally occurring undercut area above the height of contour or "presumed contact area" between two adjacent teeth.

The tooth coupling assembly 10 is preferably "C" or "U" shaped with the terminal tips engaging the natural undercuts which occur along each tooth at the cervical neck 2 and to a deeper extent between two teeth at the interproximal area 4. The tooth coupling assembly comprises a receiving means 20, a pre-attached sidecar 25, optionally an additional retaining means such as a metal spring-clip 30, a customizing dental material 40, and a transducer 50. In a preferred embodiment, sidecar 25 is integrally formed within the same thermoplastic mold as the receiving means 20 (although a different manufacturing process may join the two elements through bonding, etc.). The metal spring clip 30 is typically added later in fabrication. When fitting or customizing to a patient, the customizing dental material 40 is required.

The preferred material for the receiving means 20 is a thermoplastic or thermosetting polymer which is biocompatible and mouth safe, relatively rigid, lightweight, and inexpensive. Such plastics are well in the art and include polyvinylchloride (PVC), polyethylene, polystyrene, Polytetrafluoroethylene (PTFE), Polyetheretherketone (PEEK), Ethylene-Vinyl Acetate (EVA) and others thermoplastic or thermosetting readily available in the art.

The retaining means 30 is preferably a pre-shaped spring-wire made from one of many orthodontic-types of wire, such wire material containing stainless steel, nickel, titanium, nitinol or alloys thereof. Half-round, square, or rectangular wire (e.g., 0.025×0.020) may be used. As part of the manufacturing or assembly process of the tooth-coupling assembly 10, the wire-clip retaining means 30 is secured to the receiving means 20 with a mouth-safe glue or bonding material 32 such that the wire does not slide. The bonding material 32 thus can function as the fulcrum of the spring-arms which terminate in 31-*b* (buccal or cheek side) and 31-*l* (lingual or tongue side). An example of such an adhesive or bonding dental material 32 is Triad (Dentsply, Inter., York, Pa.). Also, a channel can be made during the thermoforming process of the receiving means 20, for fitting the wire-clip 30 into the receiving means 20 thereby needing minimal adhesion at 32. (For example, a channel of 0.027" width and 0.024" height typically will accommodate a standard, flat rectangular 0.025×0.020 orthodontic wire.)

The customizing dental material 40 can be of one of several kinds of dental materials including rigid impression compound, polyvinylsiloxane, temporary dental cements, denture pastes, and the like. The material used to fill the tooth coupling assembly 20 preferably is a poly-vinyl siloxane (PVS) addition-type dental impression material with a hardness durometer of about 40 (Shore-D scale) such as R-Si-Line Metal Bite (R-dental, Hamburg, Germany). It can also be a thermoplastic material such as dental impression compound (e.g., Denture Impression Compound, Kerr Manufacturing, Romulus, Mich.). The adhesiveness, hardness, or rigidity of the dental material should be inversely related to the rigidity of the thermoplastic of the receiving means 20 plus spring wire clip 30. For example, if the receiving means 20 and the wire clip 30 do not flex easily when placed over teeth 1, then dental material 40 can be relatively more compressible. In this example, polyvinylsiloxane is preferable over harder dental impression compound because when the tooth-coupling assembly 10 is relatively rigid and does not flex, then it can only be retrieved from the undercuts at 2 if a compressible dental material is used. By contrast, using a more flexible material for the receiving means 20 and "softer spring" for the retainer spring 30, then a more rigid material (e.g., dental compound) can be used for customizing material 40. It should be clear that by varying the materials used for the receiving means 20, the spring retainer clip 30, and the customizing filler material 40, different overall mechanical properties are achievable for the tooth coupling assembly 10. It is understood that different materials can and should be used in order to achieve differing objectives of cost, ease-of-use, ease-of-fabrication, retention, repeatability of placement, and sensitivity (for the selected accelerometer 50) without departing from the scope of the invention.

Referring to FIGS. 2 and 3, elements 21b and 21-l are the area of the receiving means that engages the natural tooth undercut 2 at the buccal (b) side and the tongue or lingual (l) side respectively. It should be understood that areas 21b and 21l run the entire mesio-distal length or front-of-mouth to back-of-mouth direction of the teeth (two teeth are included in 10). Elements 22b and 22l are "flanges" that are thermoformed to compliment the compressive areas 21b and 21l. The "flanges" are seen more easily in FIGS. 2 and 4. These "flanges" allow the patient (or dentist) to get their finger or fingernail above the receiving means 20 and more easily retrieve it from the mouth. Without the flanges 22-b and 22-l, removal of the tooth coupling assembly 10 could be difficult, particularly if there is a deep undercut at 2. Element 23b and 23l are single points located in the interproximal area between the two teeth; each is located about half-way between the molar and bicuspid teeth along an imaginary line running along 2 (in a mesio-distal or front-of-mouth to back-of-mouth direction), with element 2 being that undercut area of teeth that generally is noticeable along the gum-line. Element 4 (seen in FIG. 3) is an imaginary line connecting 23b to 23l. The design elements 21 and 23 are sized and configured to correspond to the natural constrictions that occur both at the gum-line of teeth and between adjacent teeth.

In a preferred embodiment, the tooth coupling assembly 10 also comprises a side car or transducer docking zone having elements 25, 26, and 27. As shown in FIG. 2, they are located on the buccal side of the teeth 1. The transducer docking zone is shaped and configured to correspond to the shape of the transducer to be received. As shown in FIG. 2 and FIG. 3, this zone has an outer wall 25, a floor 26, and an inner wall 27 which is also the buccal wall of the receiving means 20. The outer wall 25 is intended to flex and compress in a direction towards the tooth under the pressure of spring-wire retainer 30, or more particularly, 31b which is the buccally disposed terminal tip of spring-wire retainer 30. Element 31-l, which also has been pre-formed through metal bending, serves to add to the retention of receiving means 20 (at areas 21-l and 21-b) by reciprocating the force exerted by the tip of the spring 31-b. It is through the forcing action of the spring wire retainer 30, that transducer 50 is pressed intimately and absolutely against the inner wall 27 of the transducer docking zone. Because of this intimate and absolute contact of the transducer 50 to the receiving means 20, and the absence of gaps within the tooth coupling assembly 10, low-amplitude vibrations within the dental bone conduction pathway can be sensed and recorded accurately by transducer 50.

Figure 4:
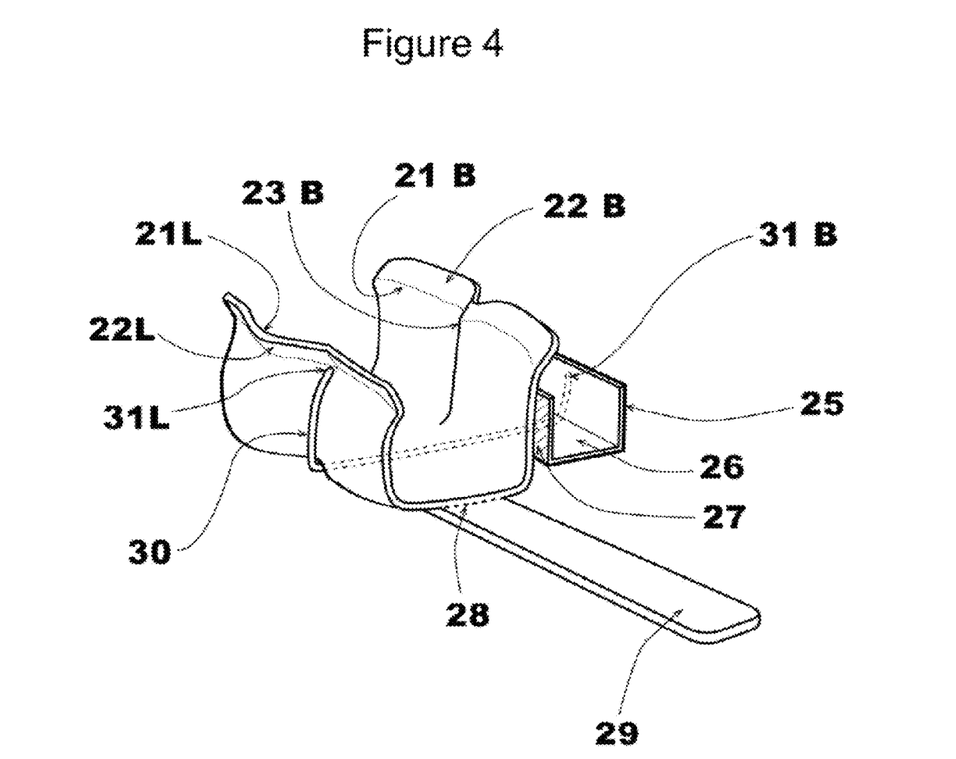
FIG. 4 is a side-perspective view of the tooth coupling assembly without the transducer or the biocompatible filler material.

FIG. 3 and FIG. 4 illustrate a top-view and side view respectively of tooth coupling assembly 10 including the "side-car" or transducer docking zone showing how the tooth coupling assembly is sized, shaped and configured to conform to the natural curvatures and undercuts of the maxillary molar and adjoining bicuspid. The receiving means 20, containing mouth safe plastics or polymers is spring-loaded into the undercut area in the gingival one-third of at least one maxillary tooth and the interproximal area between two adjacent maxillary teeth on both the buccal and lingual surfaces. The mouth safe plastics or polymers of the receiving means 20 is at least one selected from the group consisting of acrylates, methacrylates, urethanes, polyesters, polyvinylcholoride (PVC), polyethylene, polystyrene, polytetrafluoroethylene (PTFE), polyetheretherketone (PEEK), ethylene-vinyl acetate (EVA).

The receiving means 20 is preferably spring-loaded for biased retention into the undercut area in the gingival one-third of at least one maxillary tooth and the interproximal area between two adjacent maxillary teeth on both the buccal and lingual surfaces and said spring load may be achieved by use of mouth safe metals in conjunction with the thermoplastic or thermosetting materials. As an alternative embodiment, the receiving means 20 on the alternative can be rigid and made of autoclavable and reusable mouth-safe metals selected from the group consisting of stainless steel, nickel, chromium, cobalt, titanium, and alloys thereof. The receiving means further comprise flanges 22b and 22l located in a supra-gingival position relative to the tooth undercut area in the gingival one-third of at least one maxillary tooth, said flanges sized and configured for aiding in removing of said means from the mouth of a person.

In a preferred embodiment using a springy thermoplastic material, elements 21-l and 21-b and points 23-l and 23-b create retention forces for the tooth coupling assembly 10. Particularly useful for the retention of the tooth coupling assembly 10 are points 23-l and 23-b which generally conform to the interproximal areas between the two teeth (molar and bicuspid). Because retention in the interproximal area is desirable, the tooth coupling assembly is designed to include at least two teeth. Furthermore, because there is a natural curvature to each tooth at the gum-line and there is additional undercut created by two teeth (at anatomical area 4), a preferred embodiment of this invention further teaches the use of a retainer spring-wire 30 that compresses at points 31-l and 31b thus urging the assembly into undercut area 2 and interproximal area 4. Thus, spring-wire 30 helps to squeeze the pre-formed thermoplastic receiving means 20 both into the tooth neck along gum-line and into space between two adjoining teeth, and concomitantly, urges the transducer 50 towards tooth 1.

In order to facilitate placement and removal, the tooth coupling assembly 10 may be further provided with a handle 29 connected to the assembly 10 via any suitable connection or attachment means 28 such as a screw, hook, or slottable notch.

Repeatability of placement and in-situ retention of tooth-coupling assembly 10 is achieved through a combination of forces created by the spring force exerted by the thermoformed receiving means at areas 21-l, 21-b, and points 23-l, and 23-b; the spring-force exerted by the metal clip 30, specifically at points 31-l and 31-b; and pressure-fit, mechanical-fit, or adhesion, any of which occurs through selection of the appropriate dental material 40.

Element 50 is the transducer (accelerometer) which in the preferred embodiment should be slid into a tightly conforming docking zone or "sidecar" 25. The transducer senses mechanical vibrations within the dental bone conduction pathway and transmit a corresponding electrical signal through a wire 55. Wire 55 connects to a signal conditioning unit 60 (e.g., a pre-amplifier) and data recording system 70 (e.g., computer or smart-phone). These elements 60 and 70 are well known to those of ordinary skill in the art of vibration measurement and will vary with both transducer selection and modality of use. The wire 55 also serves as a safety feature to prevent potential swallowing of the tooth-clip 10.

As is generally known, depending on the type of piezoelectric transducer used, the electrical signal from the transducer typically requires a shielded lead-wire, pre-amplifier, and filtering or other signal processing. Suitable pre-amplifier design or other companion electronics necessary to optimize the signal from a specific transducer-sensor all fall within the scope of this invention.

The transducer of the present invention may be a piezoelectric, magnetostrictive, magnetoresisitive, or voice coil effect material. It can be a uni-axial (x-axis), bi-axial (x+y-axis) or tri-axial direction (x+y+z-axis) type. It may further comprise an extra-orally disposed wire or string attached to the transducer and/or receiving means.

The type of transducer used depends on the modality and the objective of recording skull vibrations via the dental bone conduction pathway. For example for cost purposes, one may use a low-cost disposable piezo-film MEMS type of transducer. For longer-term scientific analysis of a single human's breath-sounds, where the repeatability-of-placement feature of the tooth-coupling assembly is important, one may use a highly sensitive tri-axial piezoelectric based transducer (e.g., Model 339A30 from PCB-Piezotronics, Depew N.Y.). For the preferred embodiment, a lower-cost piezoelectric transducer with high sensitivity in the audio frequency range can be used, such as Model BU-1774 from Knowles Electronics (Chicago, Ill.).

It should be obvious that although the transducer 50 is re-useable, it is possible that if a low-cost single-use transducer 50 is available and desirable, then a mouth-safe glue or other potting material can entirely encase the transducer 50 within the side-car 25. In this alternative embodiment, elements 20, 30, and 50 are all pre-assembled by the manufacturer of the tooth-coupling assembly sensor. Final customization of the assembly occurs through application or use of dental material 40 at the time the tooth-coupling assembly is placed in the mouth. The final customization using internal material 40 can be performed by either a specialist, such as an audiologist, if recording of in-situ bone vibration for audiometry is desired, or alternatively, self-customization can occur if one is using the invention as the front-end sensor in a home sleep apnea study.

In an alternative embodiment for home sleep study if apnea is suspected or to be diagnosed, then the tooth-clip can be self-customized by the user through application of a particular and designated dental material 40. In this embodiment, the transducer may be pre-assembled along with other external elements of the tooth coupling assembly. The user would be provided with the internal or dental material and instructions for how to self-fit the assembly over the appropriate teeth. In this embodiment and application, the recording hardware and software system obviously would be different than if used by a technician or professional in a hospital/clinic setting. In this embodiment and application, the sensor is the front-end of a recording system and the data can be downloaded and remotely analyzed.

Figure 5:
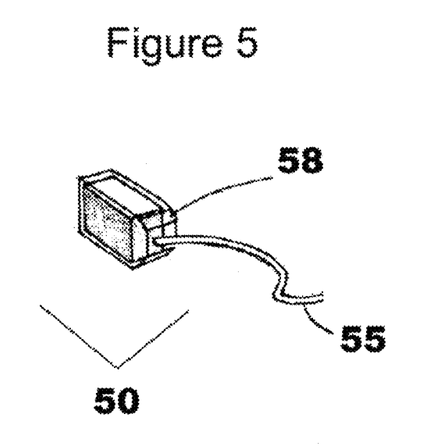
FIG. 5 illustrates a transducer (accelerometer) with disposable or permanent mouth-safe covering.

FIG. 5 shows the transducer 50 with a covering sheath 58 and safety connecting wire 55. Not shown is a plug at the terminal end of 55 that would connect into the electronic signal conditioner system 60 with further connection to a recording device 70. With a home sleep monitor, for example, this final connection of 60 to 70 can be wireless. That is, in another embodiment element 60 contains a radio transmitter that links or communicates wirelessly to the recording unit 70. The covering sheath 58 may be a disposable sanitary sheath covering the transducer and wire. Preferably sheath 58 is made of a flexible plastic whose thickness is less than 0.5 mm.

In the preferred embodiment transducer 50 is a bi-axial piezoelectric design available from one of several manufacturers of such accelerometers. The sheath 58 protects the electric transducer from the oral environment, and also if the transducer is to be used across patients, the sheath provides an impermeable and sanitary barrier. In one embodiment, the sheath 58 is fabricated of disposable thin plastic, and it can extend to cover the safety lead wire 55 to a distance well outside the mouth. The sheath should tightly fit the transducer 50 and can be secured with glue (e.g., cyanoacrylate) or alternatively twist-tied around the safety lead wire 55 and/or the tray handle 29. Alternatively, the sheath can be part of the potting material used to secure transducer 50 inside the side-car 25, if it is intended that the tooth-coupling assembly contains a disposable, single-use transducer.

The safety lead wire 55 contrasts with wireless systems. While a wireless approach is conceptually interesting, the best signal-to-noise ratio is achieved through using a hard-wire connection from the small sensor to its companion preamplifier/signal conditioner. This system design of placing elements 60 and 70 outside the mouth improves comfort, ease-of-use, and safety because the battery and other electronic components of element 60 can be larger and longer-lasting. Besides improving comfort of the overall system, this lead wire 55 also provides a safety feature because it mitigates the possibility of swallowing or choking of the tooth coupling assembly.

The tooth coupling assembly 10 is preferably prefabricated in left-side and right-side versions, and two or more sizes. By "sizes" it is intended that from a 'small size" to a "large size" the distance between 23-l and 23-b is increased by about 5 millimeters. Either a professional (e.g., audiologist), sleep lab technician (if used in a Clinic based sleep study) or the user themselves (if used in a at-home sleep study) selects a pre-assemble tooth coupling assembly 10 that contains elements 20, 30 and perhaps 50 if there was a low-cost transducer built-in ab initio. The preassembly, however, would not contain transducer 50 if the transducer was expensive such as a tri-axial accelerometer. After trial in the mouth and determination that the assembly fits snuggly, the person places the transducer (with its protective sheath) into the side-car 25. Next the user fills the receiving means 20 with the mouth safe, biocompatible dental material 40 and quickly places into their mouth, seating it fully before the material sets. The mouth-safe dental material capable of flowing around all teeth within the receiving means and then sets to a rigid or semi-rigid state so that no gaps exist between the teeth and the receiving means. The dental material may be selected from the group consisting of poly-vinyl siloxanes, polyethers, zinc-oxides, dental impression compounds, dental cements, and dental adhesives. In a preferred case of polyvinyl siloxane (R-Si-Line Metal Bite), the setting time would be about 1 minute.

At this point, if the usage of the invention is for a short time such as to measure bone vibration created by a bone oscillator from an audiometer, then the connecting wire 55 is plugged into the signal conditioner 60 and then connected to the recording system 70. If by contrast the user will be sleeping with the tooth-coupling assembly all night, then the customized assembly should be removed and handle 29 detached. Since it has been customized, it can be immediately replaced, and if desired, an additional layer of denture adhesive (e.g., Polygrip, -GlaxoSmithKline Dover, N.J.) added prior to re-seating. Once the assembly is seated, the transducer 50 is plugged into the signal conditioner 60 and recording device 70, where at 70 the vibrations within the dental bone conduction pathway are recorded, analyzed, or displayed (depending upon the hardware/software).

Accordingly, this invention also provides a method of placing a transducer in an apparatus for recording and measuring in-situ skull vibration, the method comprising the steps of selecting a receiving means that simultaneously engages the undercut area in the gingival one-third of at least one maxillary tooth and the interproximal area between two adjacent maxillary teeth, engaging said tooth and teeth on both the buccal and lingual surfaces; filling said receiving means with a dental material capable of filling any gaps between said receiving means and said at least one natural tooth, said material being capable of transmitting mechanical vibration within the dental bone conduction pathway to the receiving means and transducer; covering said transducer with a sheath and placing the covered transducer into said receiving means; connecting said transducer via a wire to a recording system disposed outside the mouth for recording electrical signals produced by the transducer. The recording system comprise a signal conditioner, pre-amplifier, amplifier, and electronic data recording device. In one embodiment, the signal conditioner is linked wirelessly to the said electronic data recording device.

The invention also provides a method of placing a transducer in an apparatus for recording and measuring in-situ skull vibration, the method comprising the steps of selecting a metallic receiving means capable of holding said transducer in intimate contact with said receiving means and at least one teeth; filling said receiving means with a dental material capable of filling any gaps between said receiving means and said at least one natural tooth, said material being capable of setting to a sufficiently rigid state in the undercut area in the gingival one-third of at least one maxillary tooth and the interproximal area between two adjacent maxillary teeth, with said material being able to compress sufficiently to allow the release and removal of said means from the mouth, said material being capable of transmitting mechanical vibration within the dental bone conduction pathway to the receiving means and transducer; connecting said transducer via a wire to a recording system disposed outside the mouth for recording electrical signals produced by the transducer.

It will be apparent to those skilled in the art that various modifications and variations can be made to the present invention without departing from the spirit or scope of the invention. Modification of the above-described assemblies and methods for carrying out the invention, combinations between different variations as practicable, and variations of aspects of the invention that are obvious to those of skill in the art are intended to be within the scope of the claims. The drawings here presented are for illustrative purposed only and are no necessarily drawn to scale. Thus, it is intended that the present invention cover the modifications and variations of this invention provided they come within the scope of the appended claims and their equivalents. Accordingly, the invention is not limited by the embodiments described above which are presented as examples only but can be modified in various ways within the scope of protection defined by the appended patent claims. All references cited in this specification are herein incorporated by reference in their entireties.

What is claimed is:

1. An apparatus for measuring and recording skull vibration in-situ comprising:
   a receiving means capable of simultaneously engaging an undercut area in a gingival one-third of at least one maxillary tooth and an interproximal area between two adjacent maxillary teeth on both a buccal surface and a lingual surface within a mouth of a user;
   a transducer coupled to said receiving means, said transducer capable of transducing mechanical vibration within a dental bone conduction pathway into electrical signals; and
   recordation hardware and software capable of receiving and processing said electrical signals from said transducer.

2. The apparatus of claim 1, further comprising a metallic spring for biasedly retaining the receiving means in the undercut area in the gingival one-third of at least one maxillary tooth and the interproximal area between two adjacent maxillary teeth on both the buccal and the lingual surfaces.

3. The apparatus of claim 2, wherein said metallic spring is configured from orthodontic spring wire containing stainless steel, nickel, titanium, or alloys of stainless steel, nickel or titanium.

4. The apparatus of claim 1, wherein said receiving means is spring-loaded into the undercut area in the gingival one-third of at least one maxillary tooth and the interproximal area between two adjacent maxillary teeth on both the buccal and the lingual surfaces and wherein said receiving means contains a mouth safe polymer.

5. The apparatus of claim 4, wherein the mouth safe polymer is selected from the group consisting of acrylates, methacrylates, urethanes, polyesters, polyvinylcholoride (PVC), polyethylene, polystyrene, polytetrafluoroethylene (PTFE), polyetheretherketone (PEEK), and ethylene-vinyl acetate (EVA).

6. The apparatus of claim 1, wherein said receiving means is spring-loaded for biased retention into the undercut area in the gingival one-third of at least one maxillary tooth and the interproximal area between two adjacent maxillary teeth on both the buccal and the lingual surfaces and wherein said receiving means is made of a mouth-safe metal.

7. The apparatus of claim 6, wherein the mouth safe metal is selected from the group consisting of stainless steel, nickel, chromium, cobalt, titanium, and alloys of stainless steel, nickel, chromium, cobalt or titanium.

8. The apparatus of claim 1, wherein said receiving means is rigid and is made of autoclavable and reusable mouth-safe metal.

9. The apparatus of claim 8, wherein the mouth safe metal is selected from the group consisting of stainless steel, nickel, chromium, cobalt, titanium, and alloys of stainless steel, nickel, chromium, cobalt or titanium.

10. The apparatus of claim 1, wherein said receiving means comprises flanges located in a supra-gingival position relative to the undercut area in the gingival one-third of at least one maxillary tooth, said flanges configured for aiding in removal of said apparatus from the mouth of the user.

11. The apparatus of claim 1, wherein said receiving means is filled with a mouth-safe dental material capable of flowing around teeth within the receiving means and setting to a rigid, semi-rigid, or adhesive state.

12. The apparatus of claim 11, wherein said dental material is selected from the group consisting of a poly-vinyl siloxane, a polyether, a zinc-oxide, a dental impression compound, a dental cement, and a dental adhesive.

13. The apparatus of claim 1, wherein said transducer comprises a piezoelectric, a magnetostrictive, a magnetoresistive, or a voice coil effect material.

14. The apparatus of claim 1, wherein said transducer is one of a uni-axial transducer, a bi-axial transducer, or a tri-axial transducer.

15. The apparatus of claim 1, further comprising an extra-orally disposed wire attached to at least one of said transducer or said receiving means.

16. The apparatus of claim 1, further comprising a disposable sanitary sheath covering said transducer.

17. The apparatus of claim 16, wherein the sheath is made of a flexible plastic having a thickness of less than about 0.5 mm.

18. A method of placing a transducer in an apparatus for recording and measuring in-situ skull vibration, the method comprising the steps of:
(a) selecting a receiving means capable of simultaneously engaging an undercut area in a gingival one-third of at least one maxillary tooth and an interproximal area between two adjacent maxillary teeth, thereby engaging said at least one maxillary tooth and said two adjacent maxillary teeth on both a buccal surface and a lingual surface within a mouth of a user, wherein a transducer is coupled to said receiving means, said transducer capable of transducing mechanical vibration within a dental bone conduction pathway into electrical signals;
(b) covering said transducer with a sheath, and placing said covered transducer into said receiving means; and
(c) electrically coupling said transducer to a recording system, said recording system capable of receiving and processing the electrical signals from said transducer, and said recording system disposed outside of the mouth of the user so that said transducer is in communication with said recording system for recording the electrical signals produced by the transducer.

19. The method of claim 18, wherein said apparatus comprises a signal conditioner, a pre-amplifier, an amplifier, and an electronic data recording device.

20. The method of claim 19, wherein said signal conditioner is linked wirelessly to said electronic data recording device.

21. The method of claim 18, wherein the receiving means contains an encapsulated transducer ab initio.

22. The apparatus of claim 1, wherein said recordation hardware comprises a signal conditioner, a pre-amplifier, an amplifier, and an electronic data recording device.

23. The apparatus of claim 22, wherein said signal conditioner is linked wirelessly to said electronic data recording device.

24. The apparatus of claim 1, wherein said transducer is encapsulated by said receiving means.

* * * * *